United States Patent
Wang (10) Patent No.: US 11,723,791 B2
(45) Date of Patent: Aug. 15, 2023

(54) DENTAL APPLIANCES FOR TREATING SLEEP DISORDERS

(71) Applicant: Dayen Peter Wang, Closter, NJ (US)

(72) Inventor: Dayen Peter Wang, Closter, NJ (US)

(*) Notice: Subject to any disclaimer, the term of this patent is extended or adjusted under 35 U.S.C. 154(b) by 0 days.

(21) Appl. No.: 17/672,280

(22) Filed: Feb. 15, 2022

(65) Prior Publication Data

US 2022/0280333 A1   Sep. 8, 2022

Related U.S. Application Data

(60) Provisional application No. 63/158,139, filed on Mar. 8, 2021.

(51) Int. Cl.
| | |
|---|---|
| *A61F 5/56* | (2006.01) |
| *A61C 7/00* | (2006.01) |
| *G16H 30/20* | (2018.01) |
| *A61C 7/36* | (2006.01) |

(52) U.S. Cl.
CPC ............. *A61F 5/566* (2013.01); *A61C 7/002* (2013.01); *A61C 7/36* (2013.01); *G16H 30/20* (2018.01)

(58) Field of Classification Search
CPC ...... A61F 5/56; A61F 5/566; A61F 2005/563; A61C 7/08; A61C 7/10; A61C 7/36; A61C 7/002; A61C 7/008; G16H 30/20
See application file for complete search history.

(56) References Cited

U.S. PATENT DOCUMENTS

| | | | |
|---|---|---|---|
| 5,313,960 A | 5/1994 | Tomasi | |
| 5,794,627 A | 8/1998 | Frantz et al. | |
| 7,730,891 B2 | 6/2010 | Lamberg | |
| 8,931,486 B2 | 1/2015 | Halstrom | |
| 2007/0079833 A1 | 4/2007 | Lamberg | |
| 2008/0099029 A1 | 5/2008 | Lamberg | |
| 2012/0010532 A1 | 1/2012 | Bolea et al. | |
| 2013/0112210 A1 | 5/2013 | Stein | |
| 2015/0238280 A1* | 8/2015 | Wu | A61C 7/002 433/24 |
| 2015/0272773 A1 | 10/2015 | Rico et al. | |
| 2017/0007363 A1* | 1/2017 | Boronkay | A61C 7/146 |
| 2020/0197214 A1 | 6/2020 | Frantz et al. | |

OTHER PUBLICATIONS

International Search Report and Written Opinion Issued in PCT Patent Application No. PCT/US2022/016440, dated Apr. 28, 2022.
Aarab et al "Effects of an Oral Appliance with Different Mandibular Protrusion Positions at a Constant Vertical Dimension on Obstructive Sleep Apnea" Clinical Oral Investigations vol. 14, pp. 339-345, 2010.
Basyuni et al "An Update on Mandibular Advancement Devices for the Treatment of Obstructive Sleep Apnoea Hypopnoea Syndrome" Journal of Thoracic Disease vol. 10, pp. S48-S56, 2018.
Dort et al "Mandibular Advancement and Obstructive Sleep Apnoea: A Method for Determining Effective Mandibular Protrusion" European Respiratory Journal vol. 27, pp. 1003-1009, 2006.

(Continued)

*Primary Examiner* — Camtu T Nguyen
(74) *Attorney, Agent, or Firm* — Cesari & McKenna, LLP (57) ABSTRACT

Disclosed are methods of preparing a dental appliance for treating a patient having obstructive sleep apnea or hypopnea. Also included are dental appliances and their uses.

20 Claims, 7 Drawing Sheets

(56) References Cited

OTHER PUBLICATIONS

Liu et al "Mandibular Advancement Devices Prevent the Adverse Cardiac Effects of Obstructive Sleep Anea-Hypopnea Syndrome (OSAHS)" Scientific Reports vol. 10, pp. 3394-3403, 2020.
Petelle et al "One-Night Mandibular Advancement Titration for Obstructive Sleep Apnea Syndrome" American Journal of Respiratory and Critical Care Medicine vol. 165, pp. 1150-1153, 2002.

* cited by examiner

TP = Target Position
A – Reference Position (0,0)
B – Maximum Protrusion Position ($X_{max}$, $Y_1$)
C – Maximum Mouth Opening Position ($X_2$, $Y_{max}$)

DENTAL APPLIANCES FOR TREATING SLEEP DISORDERS

CROSS-REFERENCE TO RELATED APPLICATIONS

This application claims the benefit of priority based on U.S. Provisional Application No. 63/158,139, filed Mar. 8, 2021, the entire content and disclosure of which is incorporated herein by reference in its entirety.

BACKGROUND

Obstructive sleep apnea-hypopnea syndrome (OSAHS) is characterized by repetitive episodes of airflow reduction (hypopnea) or cessation (apnea) during sleep due to upper airway collapse from pharyngeal narrowing.

In an obstructive sleep apnea patient, breathing repeatedly stops during sleep as throat muscles intermittently relax to the extent of completely blocking the airway. In a hypopnea patient, the airway is significantly reduced, but not completely blocked.

OSAHS affects 9-38% of adults and increases with age and obesity. See Liu et al., *Sci. Rep.* 10, 3394 (2020). According to the National Healthy Sleep Awareness Project, at least 25 million adults in the US have OSAHS. See AASM Press Releases, Sep. 29, 2014. OSAHS symptoms include excessive loud snoring, daytime sleepiness, chronic fatigue, morning headache, depression, irritability, and high blood pressure. If untreated, OSAHS decreases quality of life and can also lead to more serious conditions such as increased risks of depression, type 2 diabetes, stroke, and even sudden death in patients with heart diseases due to repeated drops in blood oxygen levels.

Nasal continuous positive airway pressure (CPAP) is the most popular treatment, in which an OSAHS patient wears a mask connecting to a machine that delivers a positive pressure and forces the airway to open during sleep. Many patients refuse CPAP for reasons including dry nasal passages, mask irritation, awakenings, machine noise, claustrophobia, and gastric distension. As such, CPAP is not well accepted among OSAHS patients.

Dental appliances have been used as an alternative to the CPAP therapy. See Petelle et al., *American Journal of Respiratory and Critical Care Medicine* 165, 1150-53 (2002); Dort et al., *European Respiratory Journal* 27, 1003-09 (2006). Worn by patients during sleep, they are intended to keep airway open either directly by forward movement of throat muscles, or indirectly by advancing the mandible. Dental appliances are less intrusive than CPAP and thus more acceptable to patients. However, their efficacy is not high, as low as 45% that of CPAP. See Basyuni et al., *J. Thorac Dis* 2018, 10 (Suppl. 1), S48-56. Recent improvements centering around design features remain unsatisfactory. See US Patent Application Publication Nos. 2013/0112210 and 2015/0272772.

There is a need to develop a high-efficacy dental appliance for treating OSAHS.

SUMMARY

This application provides methods of preparing dental appliances surprisingly effective in treating patients having OSAHS.

Accordingly, one aspect of this invention relates to a first method of preparing a dental appliance for treating a patient having obstructive sleep apnea or hypopnea. The method includes the steps of:

(i) identifying a patient having a mandibular dentition, a maxillary dentition, a tongue, an airway, and an epiglottis, in which the mandibular dentition has a central incisor and a mandibular central point located at the tip of the central incisor, (ii) optionally sedating the patient into sleep, (iii) locating a reference position (0,0) of the mandibular central point when the maxillary dentition and the mandibular dentition fit together in maximum interdigitation, (iv) determining a target position $(X_{tp}, Y_{tp})$ of the mandibular central point, into which the mandibular dentition moves so that the airway and epiglottis of the patient are open, (v) constructing the dental appliance having a lower arch section, an upper arch section, and a connecting section linking the lower arch section and the upper arch section, wherein the lower arch section conforms to the mandibular dentition, the upper arch section conforms to the maxillary dentition, $X_{tp}$ is the horizontal distance between the target position $(X_{tp}, Y_{tp})$ and the reference position (0,0), $Y_{tp}$ is the vertical distance between the target position $(X_{tp}, Y_{tp})$ and the reference position (0,0), and the lower arch section is in a position corresponding to the target position $(X_{tp}, Y_{tp})$.

Typically, $X_{tp}$ and $Y_{tp}$ are measured in millimeter (mm).

The above first method optionally further includes the following four steps of:

(vi) determining a maximum protrusive position $(X_{max})$ of the mandibular central point, into which the mandibular dentition is protruded maximally to its maximum, (vii) determining a maximum mouth opening position $(Y_{max})$ of the mandibular central point, into which the mandibular dentition is opened vertically to its maximum, (viii) calculating formulation y=ax using the target position $(X_{tp}, Y_{tp})$ and the reference position (0,0), in which a is $Y_{tp}/X_{tp}$, and (ix) determining an adjusted position $(X_{adj}, Y_{adj})$ of the mandibular central point, wherein $X_{max}$ is the horizontal distance between the reference position (0,0) and the maximum protrusive position $(X_{max})$, $Y_{max}$ is the vertical distance between the reference position (0,0) and the maximum mouth opening position $(Y_{max})$, $X_{adj}/X_{max}$ is between 1% and 80%, preferably between 2% and 75%, and more preferably between 3% and 75%, $Y_{adj}/Y_{max}$ is between 1% and 70%, preferably between 1% and 65%, and more preferably between 2% and 60%, $Y_{adj}=aX_{adj}$, and the lower arch section is moved to the adjusted position $(X_{adj}, Y_{adj})$.

The value of a is calculated by $Y_{tp}/X_{tp}$ and thus specific to the patient. For most patients, the value of a falls within the range of 0.2 to 15.

The first method can also include the steps of:

(x) obtaining a set of digital data by scanning the mandibular dentition and the maxillary dentition, (xi) registering the set of digital data into a computer system, wherein the dental appliance is constructed using the set of digital data.

Endoscopy is most often used to determine whether the airway and the epiglottis are open while the patient is asleep preferably under sedation.

Another aspect of this invention relates to a second method of preparing a dental appliance for treating a patient having OSAHS. The second method includes the steps of:
 (a) identifying a patient having a maxillary dentition, a mandibular dentition, a tongue, an airway, and an epiglottis, in which the mandibular dentition has a central incisor and a mandibular central point located at the tip of the central incisor,
 (b) locating a reference position (0,0) of the mandibular central point when the maxillary dentition and the mandibular dentition fit together in maximum interdigitation,
 (c) determining a maximum protrusive position ($X_{max}$) of the mandibular central point, into which the mandibular dentition is protruded maximally to its maximum,
 (d) determining a maximum mouth opening position ($Y_{max}$) of the mandibular central point, into which the mandibular dentition is opened vertically to its maximum,
 (e) determining a target position ($X_{tp},Y_{tp}$) of the mandibular central point, in which $Y_{tp}=bX_{tp}$, $Y_{tp}=mY_{max}$, and $X_{tp}=nX_{max}$, b being 1 to 10 (preferably 1.2 to 8, and more preferably 1.5 to 6.5), m being 5% to 70% (preferably 8% to 60%, and more preferably 12% to 50%), and n being 5% to 80% (preferably 12% to 70%, and more preferably 20% to 60%), and
 (f) constructing the dental appliance having a lower arch section, an upper arch section, and a connecting section linking the lower arch section and the upper arch section,
 wherein
  the lower arch section conforms to the mandibular dentition,
  the upper arch section conforms to the maxillary dentition,
  $X_{max}$ is the horizontal distance between the reference position (0,0) and the maximum protrusive position ($X_{max}$),
  $Y_{max}$ is the vertical distance between the reference position (0,0) and the maximum mouth opening position ($Y_{max}$),
  $X_{tp}$ is the horizontal distance between the target position ($X_{tp},Y_{tp}$) and the reference position (0,0),
  $Y_{tp}$ is the vertical distance between the target position ($X_{tp},Y_{tp}$) and the reference position (0,0), and
  the lower arch section is in a position corresponding to the target position ($X_{tp},Y_{tp}$).

The second method optionally includes the step of (g) determining an adjusted position ($X_{adj},Y_{adj}$) of the mandibular central position, in which $X_{adj}/X_{max}$ is between 5% and 80% (preferably between 6% and 75%, and more preferably between 7% and 70%), $Y_{adj}/Y_{max}$ is between 5% and 70% (preferably between 6% and 60%, and more preferably between 7% and 50%), and the lower arch section is moved to the adjusted position ($X_{adj},Y_{adj}$).

Further, the second method can include the steps of (h) obtaining a set of digital data by scanning the mandibular dentition and the maxillary dentition, and (i) registering the set of digital data into a computer system, in which the dental appliance is constructed using the set of digital data.

Also within the scope of this invention are dental appliances prepared by any of the methods described above.

Referring to the dental appliances, each of them has a lower arch section and an upper arch section, each of which has two posterior sections and an anterior section. Each dental appliance has an opening between the lower and upper arch sections at their anterior sections, and the opening has a width 20% to 50% relative to the maximum width of the tongue.

Suitable materials for making the dental appliances of this invention include durable orthodontic materials known in the art such as acrylic polymers or copolymers, acrylate polymers or copolymers, polypropylene derived materials, polyvinylchloride derived materials, polyurethane derived materials, and any combinations thereof.

The details of one or more embodiments of the invention are set forth in the description and drawings below. Other features, objects, and advantages of the invention will be apparent from the description and from the claims.

DETAILED DESCRIPTION

The dental appliance of this invention is worn by a patient to treat OSAHS. It helps keep the patient's airway and epiglottis open during sleep. This is achieved by forcing the mandibular dentition to a target position that opens the airway and at the same time provides comfortability. In the target position, the patient's lower jaw is advanced in a process commonly referred to as mandibular advancement, which moves the tongue forward, preventing the tongue from blocking the tracheal entrance. Mandibular advancement also opens airway by moving throat muscles.

The mandibular advancement is best measured by the movement of the mandibular dentition, which has two central incisors. Either one can be used to set a measuring point, defined as a mandibular central point at the tip of the central incisor. The right central incisor is often selected to define the mandibular central point. All movements of the mandibular dentition are measured using the mandibular central point.

Figure 1A:
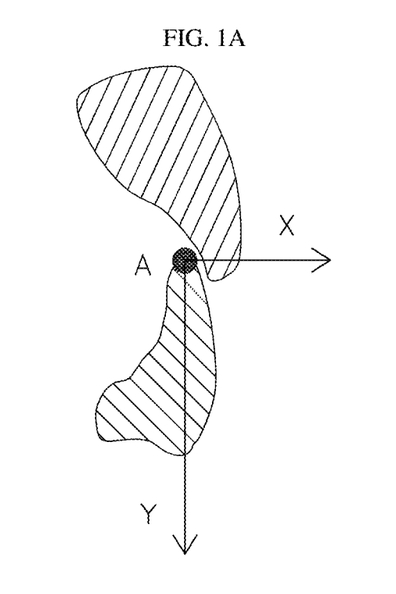
FIG. 1A shows an intercuspal position (ICP) with a reference position A (0,0), in which the mandibular dentition fits together with the maxillary dentition in maximum interdigitation. From reference position A, the mandibular dentition can move to a position (X,Y) having two components, i.e., a horizontal movement (X) and a vertical movement (Y).

In this application, the movement of mandibular advancement is quantified starting from an intercuspal position (ICP), which is the position of the mandibular dentition when it fits together with the maxillary dentition in maximum interdigitation. ICP is also known as Habitual Bite, Habitual Position, or Bite of Convenience, the position so termed as a patient is accustomed to when being asked to bite together. The mandibular central point at the ICP is assigned as a reference position A (0,0), having zero horizontal and vertical movements. See FIG. 1A.

From the ICP, the mandibular central point advances to a position (X,Y) having two components, i.e., a horizontal movement (X) and a vertical movement (Y). Usually in the unit of millimeter (mm), X and Y are the horizontal distance and the vertical distance, respectively, that the mandibular central point travels from the ICP in a mandibular advancement. Unlike the mandibular dentition, the maxillary dentition does not move during the mandibular advancement.

Figure 1B:
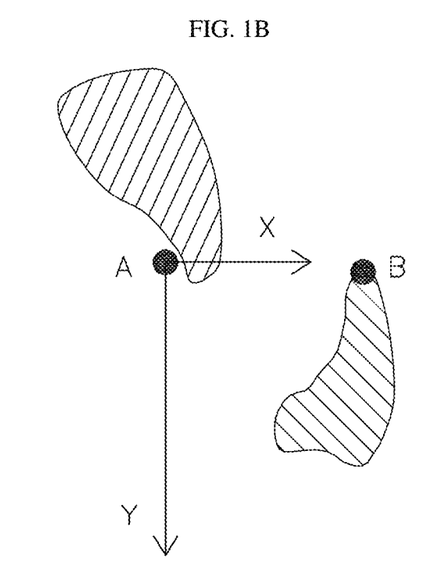
FIG. 1B demonstrates the maximum protrusion position B ($X_{max},Y_1$), in which the mandibular dentition moves forward to its maximum, reaching a maximum horizontal movement $X_{max}$ and a short vertical movement $Y_1$.
Figure 1C:
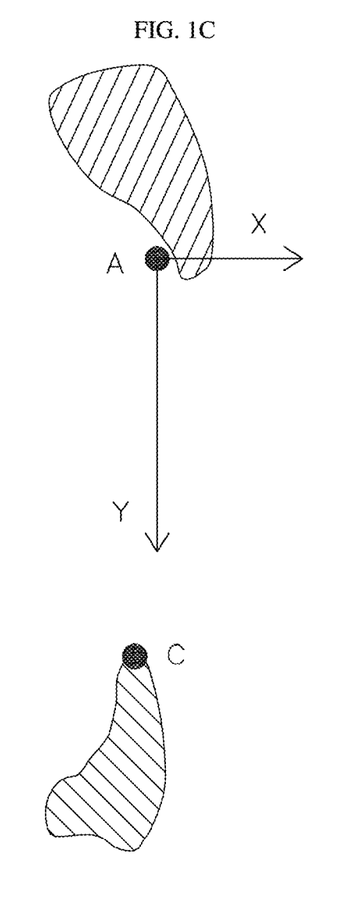
FIG. 1C shows the maximum mouth opening position C ($X_2,Y_{max}$), in which the mandibular dentition is opened vertically to its maximum, reaching a maximum vertical movement $Y_{max}$ and a short horizontal movement $X_2$.
Figure 1D:
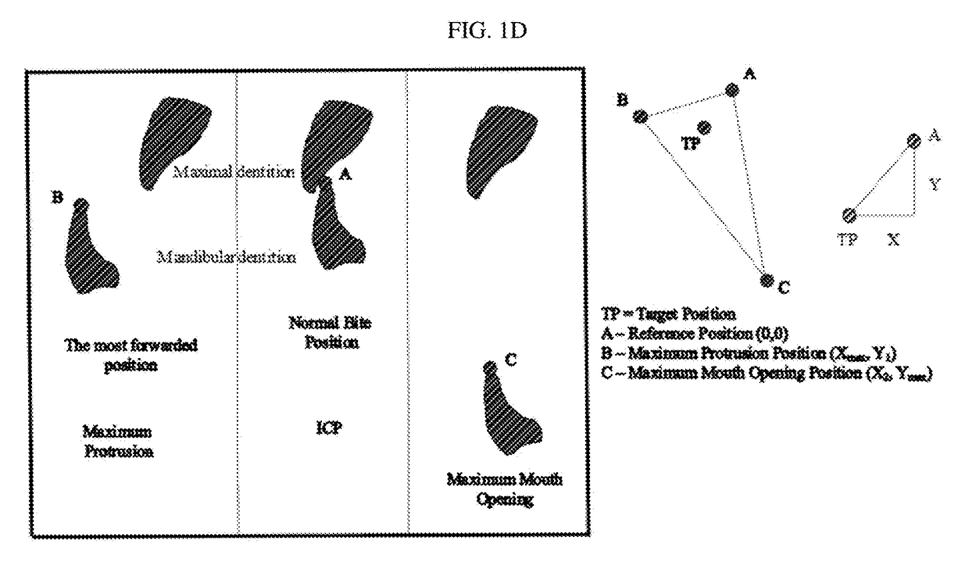
FIG. 1D illustrates that the reference position A (0,0), the maximum protrusive position B ($X_{max},Y_1$), and the maximum mouth opening position C ($X_2,Y_{max}$) form a triangle, representing the maximum area that the mandibular central point can travel.
Figure 2A:
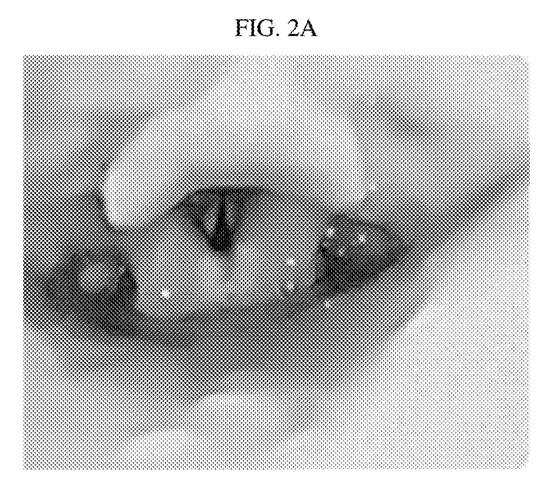
FIG. 2A is a photograph of a partially opened epiglottis and airway.
Figure 2B:
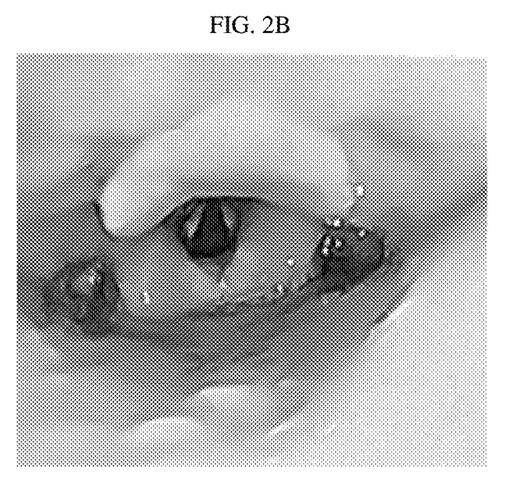
FIG. 2B is a photograph of a fully opened epiglottis and airway.
Figure 2C:
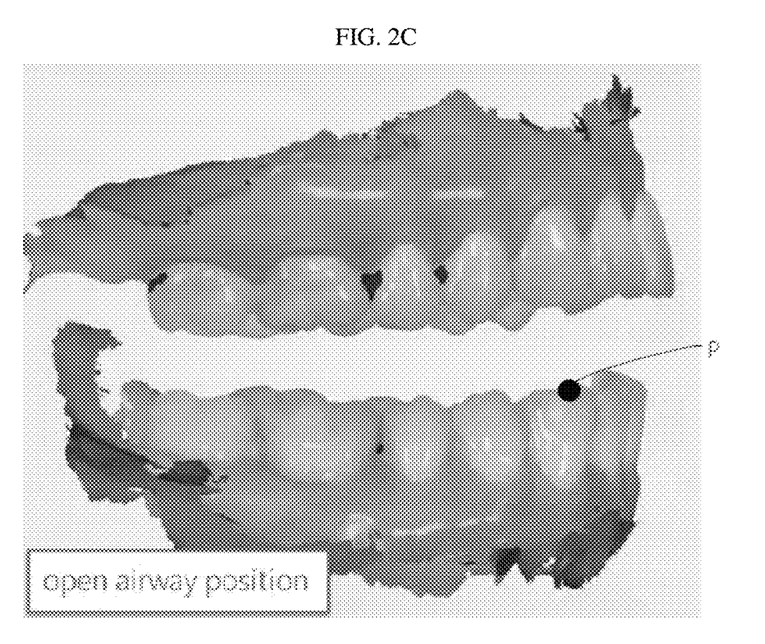
FIG. 2C shows an airway open position.
Figure 2D:
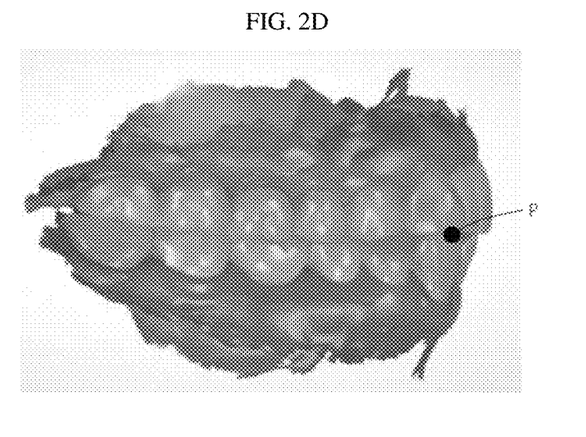
FIG. 2D shows a mouth close position.

When the mandibular dentition moves forward to its maximum, it reaches the maximum protrusive position B having a maximum horizontal movement $X_{max}$ and a short vertical movement $Y_1$. See FIG. 1B. On the other hand, when the mandibular dentition is opened vertically to its maximum, it reaches a maximum mouth opening position C having a maximum vertical movement $Y_{max}$ and a short horizontal movement $X_2$. See FIG. 1C. The reference position A (0,0), the maximum protrusive position B ($X_{max}$,$Y_1$), and the maximum mouth opening position C ($X_2$,$Y_{max}$) form a triangle ABC, representing the maximum area that the mandibular central point can travel. See FIG. 1D.

Unexpectedly, when the mandibular central point moves to a target position TP ($X_{tp}$,$Y_{tp}$), the air way is open to its maximum and the epiglottis is also open to its maximum, thus eliminating or reducing sleeping interruptions due to OSAHS.

$X_{tp}$ and $Y_{tp}$ are patient dependent. They have to be determined for each individual patient. $X_{tp}$ typically falls within the range of 0.2 mm to 10 mm (e.g., 0.3-8 mm and 0.4-6 mm). On the other hand, $Y_{tp}$ typically falls within 0.5 mm to 50 mm (e.g., 0.8-40 mm and 1-30 mm).

$X_{max}$ can be in the range of 2 mm to 25 mm (e.g., 3-20 mm and 3.5-15 mm). $Y_{max}$ can be in the range of 8 mm to 80 mm (e.g., 10-70 mm and 12-60 mm).

By way of illustration, the target position is determined by two methods. In the first method, the target position is pinpointed by endoscopy or continuous computed tomography (CT) on a patient having OSAHS. Before or after the endoscopy or CT operation, the patient's dentitions are scanned to obtain information for constructing the dental appliance. The mandibular central point and the reference position are also identified and recorded.

Scanning can be performed using X-ray, computer-aided topography (CAT scans), resonance imaging (MRI), and any other methods known in the art. Three-dimensional digital data sets can be readily obtained, which represent the mandibular dentition, the maxillary dentition, and their relative positions. The scanning data sets can also be obtained by conventional technologies, e.g., preparing a plaster cast followed by laser scanning.

The scanning data set is usually registered in a computer system, available for visualizing the dentitions, simulating their movements in a computer program, designing and modifying a dental appliance that fits onto the dentitions, and constructing the dental appliance in a three-dimensional (3-D) printer.

The scanning data set is used in combination with information regarding the target position. Endoscope and CT are two convenient technologies to identify the target position of the mandibular central point when the patient is asleep, sedated, anesthetized, or obtunded. The patient's mandibular dentition is moved protrusively or vertically while the epiglottis and the airway are monitored by endoscope or CT. The target position is reached when the airway and epiglottis are open to the maximum. The position is defined as ($X_{tp}$,$Y_{tp}$), in which $X_{tp}$ is the horizontal distance the mandibular central point travels, and $Y_{tp}$ is the vertical distance the mandibular central point travels, both from the ICP.

The target position is usually determined by trained experts (thoracic physicians or pulmonologists) to their satisfaction. FIG. 2 show (A) a partially opened epiglottis and airway, (B) a fully opened epiglottis and airway, (C) the airway open position, and (D) the mouth closing position. In determining the maximum airway opening, photographs can be taken to show the front view of the airway, areas of the airway in the photographs are then measured, and the opening corresponding to the largest area is determined as the maximum airway opening.

During the endoscope or CT operation, supplemental scanning data sets can be obtained. They are useful in simulating mandibular advancement, muscle movement, airway opening, and epiglottis positions when it is desirable to modify the dental appliance.

A standard dental appliance, i.e., a preferred embodiment of this invention, is fabricated using the target position ($X_{tp}$,$Y_{tp}$), together with the scanning data sets.

Some patients prefer modified dental appliances to standard dental appliances for comfortability or other reasons.

A modified dental appliance is constructed in the same way as the standard dental appliance except that an adjusted position ($X_{adj}$,$Y_{adj}$) is used instead of the target position ($X_{tp}$,$Y_{tp}$)

Figure 3:
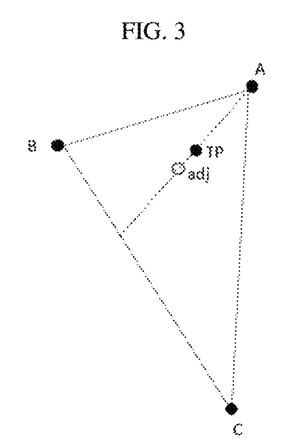
FIG. 3 shows a target position (point TP) of the mandibular central point and an adjusted position (point adj).

The adjusted position ($X_{adj}$,$Y_{adj}$) falls on the line y=ax which passes through both the reference position (0,0) and the target position ($X_{tp}$,$Y_{tp}$). See FIG. 3. In this equation, a is calculated as $Y_{tp}/X_{tp}$. In the adjusted position, the airway is opened at least 20% (e.g., at least 30%, at least 40%, and at least 50%) as compared to the maximal airway opening.

Preferably, $X_{adj}$ is in the range of 0.2 mm to 8 mm (e.g., 0.3-6 mm and 0.4-5 mm), and $Y_{adj}$ is in the range of 0.5 mm to 20 mm (e.g., 0.8-15 mm and 1-10 mm).

The modified dental appliance is then prepared using the adjusted position ($X_{adj}$,$Y_{adj}$) and the scanning data.

A serial of modified dental appliances can be prepared following the methods described above. They and the standard dental appliance are then worn by the patient one at a time to evaluate comfortability and clinical efficacy using protocols well known in the field. Evaluated on the basis of the clinical data and the wearing experience, the most suitable dental appliance is selected for everyday use.

As another illustration, a dental appliance of this invention is prepared as follows: (i) scanning a patient's oral cavity assisted by a computer system to establish a dentition model including at least a mandibular dentition and a maxillary dentition, (ii) scanning the patient's oral cavity repeatedly to identify a target position while moving the patient's mandibular dentition until the epiglottis and the airway are open to their maximum, (iii) recording the target position in the computer system, and (iv) preparing a dental appliance according to the dentition model and the target position of the mandibular dentition.

The target position thus identified requires less forward displacement than a conventional dental appliance, and therefore is more comfortable to wear by a patient.

In addition, dental appliances can be prepared by Method 2 of the invention, especially when the patient is unavailable for a study in determining the target position. As such, the second method of determining the target position involves calculation of the target position ($X_{tp}, Y_{tp}$) using the following three equations:
 (i) $Y_{tp} = bX_{tp}$, b being 1 to 10, preferably 1.2 to 8, and more preferably 1.5 to 6.5,
 (ii) $Y_{tp} = mY_{max}$, m being 5% to 70%, preferably 8% to 60%, and more preferably 12% to 50%, and
 (iii) $X_{tp} = nX_{max}$, n being 5% to 80%, preferably 12% to 70%, and more preferably 20% to 60%.

It was unexpectedly found that when the mandibular central point of a patient is rested at this target position, the airway and the epiglottis are open during sleep, thus effectively treating OSAHS. Accordingly, a standard dental appliance of this invention is constructed using the target position ($X_{tp}, Y_{tp}$) and the scanning data set collected for the mandibular and maxillary dentitions.

In the second method, the dental appliance can also be adjusted following the procedure described above as long as $X_{adj}$ and $Y_{adj}$ meet the above three equations.

$X_{tp}$, $Y_{tp}$, $X_{adj}$, $Y_{adj}$, $X_{max}$, and $Y_{max}$ can have ranges as described above.

The dental appliances of this invention can be manufactured following any known methods, such as three-divisional (3-D) printing, thermoforming, direct fabrication, machining, or any combination thereof. Stereolithography (SLA) is an exemplary 3-D printing technology in a layer-by-layer fashion using photochemical processes by which light causes monomers and oligomers to crosslink with each other to form polymers. Digital light processing (DLP) is another example, in which a digital projector is used as a light source for crosslinking monomers or oligomers. Material jetting (MJ) 3-D printers are also suitable, which dispense liquid monomer, oligomer, or resin from a printhead onto a build tray and cure it instantly under ultraviolet light.

Useful 3-D printers include those sold under the trade names of AccuFab-D1® from Shining 3D Technology Inc. (San Francisco, Calif.), NextDent® 5100 from 3D Systems (Rock Hill, S.C.), and Pro 95 from SprintRay (Los Angeles, Calif.).

Suitable materials include acrylic esters with the trade name of Ortho Clear® by NextDent® (the Netherlands), acrylic/methacrylic resin with the trade name of Freeprint® Splint by Detax GmbH & Co. (Ettlingen, Germany), and methacrylate resin with the trade name of FotoDent® Guide 405 nm by Dreve Dentamid GmbH (Unna, Germany)

The target position or adjusted position information is registered in a 3-D printer, together with the digital scanning data. Optionally, computer-aided design tools and 3-D printing programs are used to design and adjust a dental appliance of this invention. A 3-D material is dispersed from a printhead for fabricating the dental appliance according to a preset program. After or during printing, the material is hardened usually by ultraviolet light curing to ensure full crosslinking.

Alternatively, a dental appliance of this invention can be fabricated with machining from a block of material with computer numeric control (CNC) machining Additional materials that can be used in the construction of the dental appliances of the present invention include polypropylene derived materials, polyvinylchloride derived materials, and polyurethane derived materials as well as any materials capable of being safely used in the construction of a dental appliance.

Figure 4A:
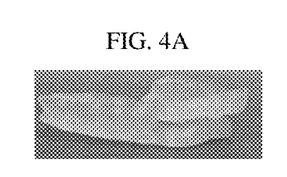
FIG. 4A is a photograph of a dental appliance of this invention, viewed from its side.
Figure 4B:
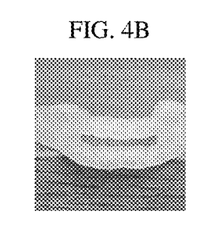
FIG. 4B is a photograph of a dental appliance of this invention, viewed from its front.
Figure 4C:
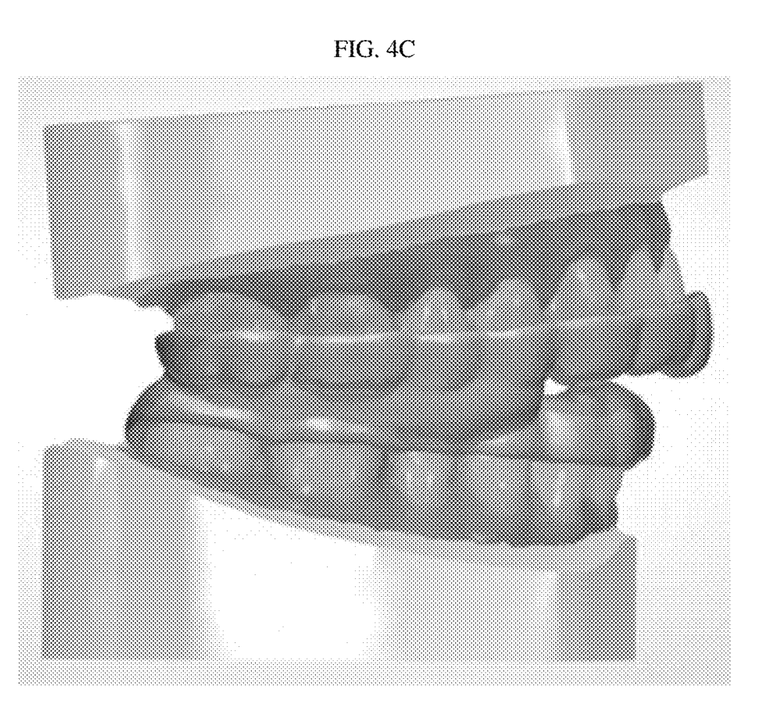
FIG. 4C shows in a model a dental appliance that is attached to the mandibular and maxillary dentitions.

The dental appliances thus prepared each have a lower arch section, an upper arch section, a connecting section linking the lower arch section and the upper arch section, and optionally an opening formed between the lower arch section, the upper arch section, and the connecting section. When worn by a patient, the lower arch section conforms to the mandibular dentition of the patient and the upper arch section conforms to the maxillary dentition. The lower arch section and the upper arch section each have (i) two posterior sections corresponding to the molars and premolars in the dentition and (ii) an anterior section corresponding to the canine and incisors. See FIGS. 4A, 4B, and 4C for an example of the dental appliance of this invention. FIG. 4A is a side view of the exemplary dental appliance. FIG. 4B is the front view. FIG. 4C shows a dental appliance attached to the mandibular and maxillary dentitions.

As illustrated in FIGS. 4A-4C, both the lower arch section and the upper arch section are symmetrical along a median plane which traverses centrally across the dental appliance. The upper arch section is positioned above the lower arch section and is coupled to the maxillary dentition. The lower arch section is coupled to the mandibular dentition. The upper arch section and the lower arch section are connected at their posterior sections but separated at their anterior sections to leave an opening that allows air to pass through and the tongue to move forward, thereby further opening the airway in the back of the mouth.

Referring to FIGS. 4A-4C again, each of the lower arch section and the upper arch section has an outer side, an inner side, and an occlusal surface. The inner sides travel along the lingual surfaces of the dentitions and are the point of contact between the appliance and the interior surfaces of the upper and lower jaws, including dentitions and gums. It meets the lingual surfaces at the anterior teeth, the posterior teeth, and the gum, wherein the anterior teeth include central incisors, lateral incisors, and canines and the posterior teeth include first and second premolars and first, second, and third molars. The outer sides of the upper and lower arch sections travel along the buccal surfaces of the dentitions and is in contact with the buccal surfaces of the teeth and the gum. The occlusal surface contacts the chewing or incisal surfaces of the teeth.

The outer side and the inner side are coupled by the occlusal surface at their posterior sections, forming a support structure for mounting the dental appliance to the dentitions.

An opening is formed from the upper right canine cusp tip to the left canine cusp tip. The width of the opening is about 20% to 50% (preferably 33%) of the maximum width of the tongue.

When worn by a patient, a dental appliance of this invention moves the mandibular dentition 0.7 mm to 6 mm horizontally and 1 mm to 15 mm vertically. This small horizontal advancement provides the patient with maximum comfort and ensures compliance with the treatment. The opening contributes to further comfort by allowing the tongue to move forward. In addition, the small vertical distance allows the patient to close their lips, another feature contributing to comfort.

The dental appliance is preferably a one-piece device, even though an adjustable design is possible with a connector that can change the position of the lower arch section vertically or horizontally relative to the upper arch section. On most occasions, the dental appliance is custom made to fit the dentitions of a patient using the target position that works most effectively and comfortably for the patient suffering from OSAHS.

The effectiveness of the dental appliance can be evaluated using any known methods. OSAHS symptoms are conventional treatment indicators, which include, but are not limited to, snoring, mouth-breathing, night cough, sleeplessness in supine position, light sleep, sleep fragmentation, nocturia, daytime sleepiness, yawn, headache, chest tightness, hoarse voice, irritating throat, excessive mucus, swallowing difficulty, breathing difficulty, heartburn, chest pain, nausea, hypertension, and nocturnal hypoxemia. Those symptoms can be self-reported in a questionnaire for evaluating the severity of the apnea or hypopnea and the treatment effectiveness. The apnea-hypopnea index (AHI) and oxygen desaturation levels are also commonly used to indicate the severity. The AHI is the number of apneas or hypopneas occurred per hour of sleep and is expressed as the number of events per hour. A mild apnea or hypopnea has an AHI of 5 or greater but less than 15 and has an oxygen desaturation level of 90% or greater. A moderate apnea or hypopnea has an AHI of 15 or greater but less than 30 and has an oxygen desaturation level of 80% to 89%. A severe apnea or hypopnea has an AHI of 30 or greater and has an oxygen desaturation level of less than 80%.

Without further elaboration, it is believed that one skilled in the art can, based on the disclosure herein, utilize the present disclosure to its fullest extent. The following specific examples are, therefore, to be construed as merely descriptive, and not limitative of the remainder of the disclosure in any way whatsoever. All publications and patent documents cited herein are incorporated by reference in their entirety.

The dental appliances in Table 1 below were prepared following Method 1 described above. Adjusted dental appliance, $X_{max}$, $Y_{max}$, $X_{tp}$, $Y_{tp}$ are all defined above.

Table 2 below shows examples of dental appliances of this invention prepared following Method 2.

TABLE 1

| | Dental appliance prepared according to Method 1 | | | | | | Adjusted dental appliance | | | |
|---|---|---|---|---|---|---|---|---|---|---|
| NO. | $X_{tp}$, mm | $Y_{tp}$, mm | $X_{max}$, mm | $Y_{max}$, mm | $X_{tp}/X_{max}$ | $Y_{tp}/Y_{max}$ | $X_{adj}$, mm | $Y_{adj}$, mm | $X_{adj}/X_{max}$ | $Y_{adj}/Y_{max}$ |
| 1 | 3 | 5.7 | 10.3 | 18.5 | 29% | 31% | 3.1 | 6 | 30% | 32% |
| 2 | 1.3 | 4.7 | 13.7 | 50.8 | 9% | 9% | 2.7 | 10 | 20% | 20% |
| 3 | 1.9 | 24.2 | 7.8 | 43 | 24% | 56% | 0.6 | 8 | 8% | 19% |
| 4 | 0.4 | 1.9 | 4.1 | 39 | 10% | 5% | 1.1 | 5 | 27% | 13% |
| 5 | 1.2 | 2.5 | 7.4 | 35.2 | 16% | 7% | 1.2 | 2.5 | 16% | 7% |
| 6 | 4 | 5.8 | 5.5 | 41.8 | 74% | 14% | 4.2 | 6 | 77% | 14% |
| 7 | 1.4 | 2.7 | 4.5 | 35.4 | 30% | 8% | 3 | 6 | 66% | 17% |
| 8 | 1.7 | 4.3 | 10.3 | 44.8 | 16% | 9% | 2.7 | 7 | 26% | 16% |
| 9 | 0.7 | 1.5 | 5.7 | 44 | 11% | 3% | 3.6 | 8 | 62% | 18% |
| 10 | 3.6 | 8.5 | 12.1 | 46 | 29% | 18% | 3.6 | 8.5 | 29% | 18% |

TABLE 2

| | Dental Appliance prepared according to Method 2 | | | | | | Adjusted dental appliance | | | |
|---|---|---|---|---|---|---|---|---|---|---|
| NO. | $X_{tp}$, mm | $Y_{tp}$, mm | $X_{max}$, mm | $Y_{max}$, mm | $X_{tp}/X_{max}$ | $Y_{tp}/Y_{max}$ | $X_{adj}$, mm | $Y_{adj}$, mm | $X_{adj}/X_{max}$ | $Y_{adj}/Y_{max}$ |
| 11 | 1.2 | 4.4 | 4.2 | 26.4 | 29% | 17% | 2.7 | 10 | 65% | 38% |
| 12 | 2.4 | 2.1 | 8.3 | 12.3 | 29% | 17% | 1 | 1 | 12% | 8% |
| 13 | 1.6 | 9.5 | 6.3 | 27.2 | 25% | 35% | 1.6 | 9.5 | 25% | 35% |
| 14 | 3.3 | 8.4 | 6.7 | 19.1 | 50% | 44% | 3.3 | 8.4 | 50% | 44% |
| 15 | 2.9 | 8.4 | 10.2 | 49.7 | 29% | 17% | 3.5 | 10 | 35% | 20% |
| 16 | 2.6 | 7.1 | 8.9 | 42.2 | 29% | 17% | 3.1 | 8.5 | 35% | 20% |
| 17 | 5.6 | 8.9 | 11.9 | 40.6 | 47% | 22% | 5 | 8 | 42% | 20% |
| 18 | 2.1 | 7.3 | 7.2 | 43.5 | 29% | 17% | 2.8 | 10 | 40% | 23% |
| 19 | 1.1 | 5.6 | 3.9 | 36.9 | 28% | 15% | 1.6 | 8.5 | 42% | 23% |
| 20 | 2.4 | 6.4 | 8.3 | 38 | 29% | 17% | 2.5 | 6.5 | 29% | 17% |
| 21 | 2.6 | 7.7 | 8.9 | 46 | 29% | 17% | 2 | 6 | 22% | 13% |
| 22 | 2.9 | 8.9 | 8.5 | 37 | 34% | 24% | 2.9 | 9 | 34% | 24% |
| 23 | 2.6 | 10.8 | 7.6 | 46.9 | 34% | 23% | 2.4 | 10 | 31% | 21% |
| 24 | 1.4 | 7.3 | 4.8 | 43.7 | 29% | 17% | 1.9 | 10 | 39% | 23% |
| 25 | 2.5 | 6.6 | 8.9 | 46.2 | 28% | 14% | 3.2 | 8.5 | 36% | 18% |
| 26 | 2.3 | 6 | 7.8 | 35.9 | 29% | 17% | 2.3 | 6.1 | 29% | 17% |
| 27 | 1.8 | 6.4 | 6.3 | 37.9 | 29% | 17% | 2.3 | 8 | 36% | 21% |
| 28 | 1.7 | 5.5 | 5.8 | 32.8 | 29% | 17% | 1.7 | 5.5 | 29% | 17% |
| 29 | 1.2 | 6.9 | 4 | 41.2 | 29% | 17% | 1.4 | 8 | 33% | 19% |
| 30 | 1.8 | 6 | 6.8 | 42.2 | 27% | 14% | 1.8 | 6 | 27% | 14% |

Unexpectedly, the dental appliances in Tables 1 and 2 above effectively cured or alleviated obstructive sleep apnea or hypopnea.

OTHER EMBODIMENTS

All of the features disclosed in this specification may be combined in any combination. Each feature disclosed in this specification may be replaced by an alternative feature serving the same, equivalent, or similar purpose. Unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of preparing a dental appliance for treating a patient having obstructive sleep apnea or hypopnea, the method comprising the steps of:
    (i) identifying the patient having a mandibular dentition, a maxillary dentition, a tongue, an airway, and an epiglottis, in which the mandibular dentition has a central incisor and a mandibular central point located at the tip of the central incisor,
    (iii) locating a reference position (0,0) of the mandibular central point when the maxillary dentition and the mandibular dentition fit together in maximum interdigitation,
    (iv) determining a target position $(X_{tp}, Y_{tp})$ of the mandibular central point, into which the mandibular dentition moves so that the airway and epiglottis of the patient are open,
    (v) constructing the dental appliance having a lower arch section, an upper arch section, and a connecting section linking the lower arch section and the upper arch section,
    (vi) determining a maximum protrusive position $(X_{max})$ of the mandibular central point, into which the mandibular dentition is protruded horizontally to its maximum,
    (vii) determining a maximum mouth opening position $(Y_{max})$ of the mandibular central point, into which the mandibular dentition is opened vertically to its maximum,
    (viii) calculating formulation y=ax using the target position $(X_{tp}, Y_{tp})$ and the reference position (0,0), in which a is $Y_{tp}/X_{tp}$, and
    (ix) determining an adjusted position $(X_{adj}, Y_{adj})$ of the mandibular central position,
    wherein
    the lower arch section conforms to the mandibular dentition,
    the upper arch section conforms to the maxillary dentition,
    $X_{tp}$ is the horizontal distance between the target position $(X_{tp}, Y_{tp})$ and the reference position (0,0),
    $Y_{tp}$ is the vertical distance between the target position $(X_{tp}, Y_{tp})$ and the reference position (0,0),
    $X_{max}$ is the horizontal distance between the reference position (0,0) and the maximum protrusive position $(X_{max})$,
    $Y_{max}$ is the vertical distance between the reference position (0,0) and the maximum mouth opening position $(Y_{max})$,
    $X_{adj}/X_{max}$ is between 1% and 80%,
    $Y_{adj}/Y_{max}$ is between 1% and 70%,
    $Y_{adj}=aX_{adj}$, and
    the lower arch section is in a position corresponding to the adjusted position $(X_{adj}, Y_{adj})$.

2. The method of claim 1, further comprising step (ii): sedating the patient into sleep before step (iii).

3. The method of claim 2, further comprising
    (x) obtaining a set of digital data by scanning the mandibular dentition and the maxillary dentition,
    (xi) registering the set of digital data into a computer system,
    wherein the dental appliance is constructed using the set of digital data.

4. The method of claim 3, wherein endoscopy is used to determine whether the airway and the epiglottis are open.

5. The method of claim 4, wherein each of the lower arch section and the upper arch section has two posterior sections and an anterior section, the dental appliance has an opening between the lower and upper arch sections at their anterior sections, and the opening has a width 20% to 50% relative to the maximum width of the tongue.

6. The method of claim 5, wherein the dental appliance is made of an acrylic polymer or copolymer, an acrylate polymer or copolymer, or a combination thereof.

7. The method of claim 1, further comprising
    (x) obtaining a set of digital data by scanning the mandibular dentition and the maxillary dentition,
    (xi) registering the set of digital data into a computer system,
    wherein the dental appliance is constructed using the set of digital data.

8. The method of claim 1, wherein endoscopy is used to determine whether the airway and epiglottis of the patient are open.

9. The method of claim 1, wherein each of the lower arch section and the upper arch section has two posterior sections and an anterior section, the dental appliance has an opening between the lower and upper arch sections at their anterior sections, and wherein the opening has a width 20% to 50% relative to the maximum width of the tongue.

10. The method of claim 1, wherein the dental appliance is made of an acrylic polymer or copolymer, an acrylate polymer or copolymer, or a combination thereof.

11. A dental appliance prepared by the method of claim 1.

12. A method of preparing a dental appliance for treating a patient having obstructive sleep apnea or hypopnea, the method comprising the steps of:
    (a) identifying the patient having a maxillary dentition, a mandibular dentition, a tongue, an airway, and an epiglottis, in which the mandibular dentition has a central incisor and a mandibular central point located at the tip of the central incisor,
    (b) locating a reference position (0,0) of the mandibular central point when the maxillary dentition and the mandibular dentition fit together in maximum interdigitation,
    (c) determining a maximum protrusive position $(X_{max})$ of the mandibular central point, into which the mandibular dentition is protruded horizontally to its maximum,
    (d) determining a maximum mouth opening position $(Y_{max})$ of the mandibular central point, into which the mandibular dentition is opened vertically to its maximum,
    (e) determining a target position $(X_{tp}, Y_{tp})$ of the mandibular central point, in which $Y_{tp}=bX_{tp}$, $Y_{tp}=mY_{max}$, and $X_{tp}=nX_{max}$, b being 1 to 10, m being 5% to 70%, and n being 5% to 80%, and (f) constructing the dental appliance having a lower arch section, an upper arch section, and a connecting section linking the lower arch section and the upper arch section, wherein the lower arch section conforms to the mandibular dentition, the upper arch section conforms to the maxillary dentition, $X_{max}$ is the horizontal distance between the reference position (0,0) and the maximum protrusive position $(X_{max})$, $Y_{max}$ is the vertical distance between the reference position (0,0) and the maximum mouth opening position $(Y_{max})$, $X_{tp}$ is the horizontal distance between the target position $(X_{tp}, Y_{tp})$ and the reference position (0,0), $Y_{tp}$ is the vertical distance between the target position $(X_{tp}, Y_{tp})$ and the reference position (0,0), and the lower arch section is in a position corresponding to the target position $(X_{tp}, Y_{tp})$.

13. The method of claim 12, further comprising:

(g) determining an adjusted position $(X_{adj}, Y_{adj})$ of the mandibular central position, wherein $X_{adj}/X_{max}$ is between 5% and 80%, $Y_{adj}/Y_{max}$ is between 5% and 70%, and the lower arch section is moved to the adjusted position $(X_{adj}, Y_{adj})$.

14. The method of claim 13, further comprising:

(h) obtaining a set of digital data by scanning the mandibular dentition and the maxillary dentition, (i) registering the set of digital data into a computer system, wherein the dental appliance is constructed using the set of digital data.

15. The method of claim 14, wherein each of the lower arch section and the upper arch section has two posterior sections and an anterior section, the dental appliance has an opening between the lower and upper arch sections at their anterior sections, and wherein the opening has a width 20% to 50% relative to the maximum width of the tongue.

16. The method of claim 15, wherein the dental appliance is made of an acrylic polymer or copolymer, an acrylate polymer or copolymer, or a combination thereof.

17. The method of claim 12, further comprising (h) obtaining a set of digital data by scanning the mandibular dentition and the maxillary dentition, (i) registering the set of digital data into a computer system, wherein the dental appliance is constructed using the set of digital data.

18. The method of claim 12, wherein each of the lower arch section and the upper arch section has two posterior sections and an anterior section, the dental appliance has an opening between the lower arch and the upper arch at their anterior sections, and wherein the opening has a width 20% to 50% relative to the maximum width of the tongue.

19. The method of claim 12, wherein the dental appliance is made of an acrylic polymer or copolymer, an acrylate polymer or copolymer, or a combination thereof.

20. A dental appliance prepared by the method of claim 12.

* * * * *